US012527616B2

(12) United States Patent
Kerr et al.

(10) Patent No.: US 12,527,616 B2
(45) Date of Patent: Jan. 20, 2026

(54) SURGICAL FORCEPS INCLUDING REPOSABLE END EFFECTOR ASSEMBLIES

(71) Applicant: Covidien LP, Mansfield, MA (US)

(72) Inventors: Duane E. Kerr, Loveland, CO (US); James D. Allen, IV, Broomfield, CO (US); Robert M. Sharp, Boulder, CO (US); William H. Nau, Jr., Longmont, CO (US)

(73) Assignee: Covidien LP, Mansfield, MA (US)

( * ) Notice: Subject to any disclaimer, the term of this patent is extended or adjusted under 35 U.S.C. 154(b) by 348 days.

(21) Appl. No.: 18/116,478

(22) Filed: Mar. 2, 2023

(65) Prior Publication Data

US 2023/0200886 A1 Jun. 29, 2023

Related U.S. Application Data

(62) Division of application No. 16/559,982, filed on Sep. 4, 2019, now Pat. No. 11,596,465, which is a division (Continued)

(51) Int. Cl.

| | |
|---|---|
| ***A61B 18/14*** | (2006.01) |
| ***A61B 17/29*** | (2006.01) |
| ***A61B 17/295*** | (2006.01) |

(52) U.S. Cl.

CPC .......... *A61B 18/1445* (2013.01); *A61B 17/29* (2013.01); *A61B 17/295* (2013.01);

(Continued)

(58) Field of Classification Search

CPC .. A61B 2017/07214; A61B 2017/2931; A61B 18/1445

See application file for complete search history.

(56) References Cited

U.S. PATENT DOCUMENTS

| | | | |
|---|---|---|---|
| D249,549 | S | 9/1978 | Pike |
| D263,020 | S | 2/1982 | Rau, III |

(Continued)

FOREIGN PATENT DOCUMENTS

| | | | |
|---|---|---|---|
| CN | 201299462 | Y | 9/2009 |
| DE | 2415263 | A1 | 10/1975 |

(Continued)

OTHER PUBLICATIONS

Chinese office action issued in corresponding application No. 201310303960.0 dated Jul. 18, 2016.

(Continued)

*Primary Examiner* — Ronald Hupczey, Jr.

(57) ABSTRACT

A surgical forceps including a housing having a movable handle coupled thereto and movable between an initial position and a compressed position is disclosed. A drive bar is operably coupled to the movable handle such that movement of the movable handle between the initial and compressed positions effects longitudinal translation of the drive bar. The drive bar further includes a coupling member disposed at a distal end thereof. An end effector assembly includes first and second jaw members movable between spaced-apart and approximated positions. Each jaw member defines a cam slot. A cam pin is slidably disposed within the cam slot of each of the jaw members. The coupling member is configured to releasably engage the cam pin such that movement of the movable handle between the initial position and the compressed position effects movement of the jaw members between the spaced-apart position and the approximated position.

19 Claims, 5 Drawing Sheets

Related U.S. Application Data of application No. 15/019,490, filed on Feb. 9, 2016, now Pat. No. 10,413,353, which is a division of application No. 13/936,510, filed on Jul. 8, 2013, now Pat. No. 9,301,798.

(60) Provisional application No. 61/673,308, filed on Jul. 19, 2012.

(52) U.S. Cl.
CPC ................ *A61B 2017/2931* (2013.01); *A61B 2017/2936* (2013.01); *A61B 2017/294* (2013.01); *A61B 2017/2947* (2013.01); *A61B 2018/1455* (2013.01); *A61B 2018/1495* (2013.01)

(56) References Cited

U.S. PATENT DOCUMENTS

| | | | |
|---|---|---|---|
| D295,893 S | | 5/1988 | Sharkany et al. |
| D295,894 S | | 5/1988 | Sharkany et al. |
| D298,353 S | | 11/1988 | Manno |
| D299,413 S | | 1/1989 | DeCarolis |
| 5,176,699 A | | 1/1993 | Markham |
| D343,453 S | | 1/1994 | Noda |
| D348,930 S | | 7/1994 | Olson |
| D349,341 S | | 8/1994 | Lichtman et al. |
| D354,564 S | | 1/1995 | Medema |
| D358,887 S | | 5/1995 | Feinberg |
| 5,499,992 A | | 3/1996 | Meade et al. |
| 5,582,617 A | | 12/1996 | Klieman et al. |
| D384,413 S | | 9/1997 | Zlock et al. |
| H1745 H | | 8/1998 | Paraschac |
| 5,792,165 A | | 8/1998 | Klieman et al. |
| 5,810,865 A | | 9/1998 | Koscher et al. |
| D402,028 S | | 12/1998 | Grimm et al. |
| D408,018 S | | 4/1999 | McNaughton |
| 5,893,874 A | | 4/1999 | Bourque et al. |
| D416,089 S | | 11/1999 | Barton et al. |
| D424,694 S | | 5/2000 | Tetzlaff et al. |
| D425,201 S | | 5/2000 | Tetzlaff et al. |
| 6,059,776 A | | 5/2000 | Gatto |
| 6,086,606 A | * | 7/2000 | Knodel ................ A61B 17/29 606/174 |
| H1904 H | | 10/2000 | Yates et al. |
| 6,293,954 B1 | | 9/2001 | Fogarty et al. |
| D449,886 S | | 10/2001 | Tetzlaff et al. |
| D453,923 S | | 2/2002 | Olson |
| D454,951 S | | 3/2002 | Bon |
| D457,958 S | | 5/2002 | Dycus et al. |
| D457,959 S | | 5/2002 | Tetzlaff et al. |
| H2037 H | | 7/2002 | Yates et al. |
| D465,281 S | | 11/2002 | Lang |
| D466,209 S | | 11/2002 | Bon |
| D493,888 S | | 8/2004 | Reschke |
| D496,997 S | | 10/2004 | Dycus et al. |
| D499,181 S | | 11/2004 | Dycus et al. |
| D502,994 S | | 3/2005 | Blake, III |
| D509,297 S | | 9/2005 | Wells |
| 7,055,413 B1 | | 6/2006 | Wang |
| D525,361 S | | 7/2006 | Hushka |
| D531,311 S | | 10/2006 | Guerra et al. |
| D533,274 S | | 12/2006 | Visconti et al. |
| D533,942 S | | 12/2006 | Kerr et al. |
| D535,027 S | | 1/2007 | James et al. |
| D538,932 S | | 3/2007 | Malik |
| D541,418 S | | 4/2007 | Schechter et al. |
| 7,208,005 B2 | | 4/2007 | Frecker et al. |
| D541,611 S | | 5/2007 | Aglassinge |
| D541,938 S | | 5/2007 | Kerr et al. |
| D545,432 S | | 6/2007 | Watanabe |
| D547,154 S | | 7/2007 | Lee |
| 7,306,597 B2 | | 12/2007 | Manzo |
| D564,662 S | | 3/2008 | Moses et al. |
| D567,943 S | | 4/2008 | Moses et al. |
| D575,395 S | | 8/2008 | Hushka |
| D575,401 S | | 8/2008 | Hixson et al. |
| 7,435,249 B2 | | 10/2008 | Buysse et al. |
| D582,038 S | | 12/2008 | Swoyer et al. |
| D617,900 S | | 6/2010 | Kingsley et al. |
| D617,901 S | | 6/2010 | Unger et al. |
| D617,902 S | | 6/2010 | Twomey et al. |
| D617,903 S | | 6/2010 | Unger et al. |
| D618,798 S | | 6/2010 | Olson et al. |
| D621,503 S | | 8/2010 | Otten et al. |
| D627,462 S | | 11/2010 | Kingsley |
| D628,289 S | | 11/2010 | Romero |
| D628,290 S | | 11/2010 | Romero |
| D630,324 S | | 1/2011 | Reschke |
| D649,249 S | | 11/2011 | Guerra |
| D649,643 S | | 11/2011 | Allen, IV et al. |
| D661,394 S | | 6/2012 | Romero et al. |
| 8,251,996 B2 | | 8/2012 | Hushka et al. |
| 8,647,362 B2 | | 2/2014 | Griego |
| 8,679,140 B2 | | 3/2014 | Butcher |
| RE44,834 E | | 4/2014 | Dumbauld et al. |
| 8,827,996 B2 | | 9/2014 | Scott et al. |
| 8,894,674 B2 | | 11/2014 | Balanev et al. |
| 8,968,311 B2 | | 3/2015 | Allen, IV et al. |
| 10,413,353 B2 | | 9/2019 | Kerr et al. |
| 2002/0188220 A1 | | 12/2002 | Krzyzanowski |
| 2004/0054364 A1 | | 3/2004 | Aranyi et al. |
| 2004/0186513 A1 | | 9/2004 | Dworschak et al. |
| 2005/0131396 A1 | | 6/2005 | Stanczak et al. |
| 2006/0161190 A1 | | 7/2006 | Gadberry et al. |
| 2007/0027469 A1 | | 2/2007 | Smith et al. |
| 2007/0073341 A1 | | 3/2007 | Smith et al. |
| 2008/0004656 A1 | | 1/2008 | Livneh |
| 2008/0091189 A1 | | 4/2008 | Carlton |
| 2009/0182327 A1 | | 7/2009 | Unger |
| 2010/0057085 A1 | | 3/2010 | Holcomb et al. |
| 2011/0060333 A1 | | 3/2011 | Mueller |
| 2011/0184405 A1 | | 7/2011 | Mueller |
| 2012/0065466 A1 | | 3/2012 | Slater |
| 2013/0245623 A1 | | 9/2013 | Twomey |
| 2013/0247343 A1 | | 9/2013 | Horner et al. |
| 2013/0253489 A1 | | 9/2013 | Nau, Jr. et al. |
| 2013/0255063 A1 | | 10/2013 | Hart et al. |
| 2013/0267948 A1 | | 10/2013 | Kerr et al. |
| 2013/0267949 A1 | | 10/2013 | Kerr |
| 2013/0274736 A1 | | 10/2013 | Garrison |
| 2013/0282010 A1 | | 10/2013 | Mckenna et al. |
| 2013/0289561 A1 | | 10/2013 | Waaler et al. |
| 2013/0296854 A1 | | 11/2013 | Mueller |
| 2013/0296922 A1 | | 11/2013 | Allen, IV et al. |
| 2013/0296923 A1 | | 11/2013 | Twomey et al. |
| 2013/0304058 A1 | | 11/2013 | Kendrick |
| 2013/0304059 A1 | | 11/2013 | Allen, IV et al. |
| 2013/0304066 A1 | | 11/2013 | Kerr et al. |
| 2013/0310832 A1 | | 11/2013 | Kerr et al. |
| 2013/0325057 A1 | | 12/2013 | Larson et al. |
| 2013/0331837 A1 | | 12/2013 | Larson |
| 2013/0338666 A1 | | 12/2013 | Bucciaglia et al. |
| 2013/0338693 A1 | | 12/2013 | Kerr et al. |
| 2013/0345701 A1 | | 12/2013 | Allen, IV et al. |
| 2013/0345706 A1 | | 12/2013 | Garrison |
| 2013/0345735 A1 | | 12/2013 | Mueller |
| 2014/0005663 A1 | | 1/2014 | Heard et al. |
| 2014/0005666 A1 | | 1/2014 | Moua et al. |
| 2014/0025052 A1 | | 1/2014 | Nau, Jr. et al. |
| 2014/0025053 A1 | | 1/2014 | Nau, Jr. et al. |
| 2014/0025059 A1 | | 1/2014 | Kerr |
| 2014/0025060 A1 | | 1/2014 | Kerr |
| 2014/0025066 A1 | | 1/2014 | Kerr |
| 2014/0025067 A1 | | 1/2014 | Kerr et al. |
| 2014/0025070 A1 | | 1/2014 | Kerr et al. |
| 2014/0025073 A1 | | 1/2014 | Twomey et al. |
| 2014/0031821 A1 | | 1/2014 | Garrison |
| 2014/0031860 A1 | | 1/2014 | Stoddard et al. |
| 2014/0046323 A1 | | 2/2014 | Payne et al. |
| 2014/0066910 A1 | | 3/2014 | Nau, Jr. |
| 2014/0066911 A1 | | 3/2014 | Nau, Jr. |

(56) References Cited

U.S. PATENT DOCUMENTS

| | | | |
|---|---|---|---|
| 2014/0074091 A1 | 3/2014 | Arya et al. | |
| 2014/0100564 A1 | 4/2014 | Garrison | |
| 2014/0100568 A1 | 4/2014 | Garrison | |

FOREIGN PATENT DOCUMENTS

| | | | |
|---|---|---|---|
| DE | 02514501 | A1 | 10/1976 |
| DE | 2627679 | A1 | 1/1977 |
| DE | 03423356 | C2 | 6/1986 |
| DE | 03612646 | A1 | 4/1987 |
| DE | 8712328 | U1 | 2/1988 |
| DE | 4303882 | C2 | 2/1995 |
| DE | 4403252 | A1 | 8/1995 |
| DE | 19515914 | C1 | 7/1996 |
| DE | 19506363 | A1 | 8/1996 |
| DE | 29616210 | U1 | 11/1996 |
| DE | 19608716 | C1 | 4/1997 |
| DE | 19751106 | A1 | 5/1998 |
| DE | 19738457 | A1 | 3/1999 |
| DE | 19751108 | A1 | 5/1999 |
| DE | 19946527 | C1 | 7/2001 |
| DE | 10031773 | A1 | 11/2001 |
| DE | 10045375 | A1 | 4/2002 |
| DE | 20121161 | U1 | 4/2002 |
| DE | 202007009165 | U1 | 8/2007 |
| DE | 202007009317 | U1 | 8/2007 |
| DE | 202007009318 | U1 | 8/2007 |
| DE | 202007016233 | U1 | 1/2008 |
| DE | 102004026179 | B4 | 1/2009 |
| DE | 102008018406 | B3 | 7/2009 |
| EP | 1159926 | A2 | 12/2001 |
| EP | 1281878 | A1 | 2/2003 |
| EP | 2258297 | A1 | 12/2010 |
| EP | 2399538 | A2 | 12/2011 |
| JP | 61501068 | A | 5/1986 |
| JP | H1024051 | | 1/1989 |
| JP | 6502328 | | 3/1992 |
| JP | 65502328 | | 3/1992 |
| JP | 55106 | | 1/1993 |
| JP | H0540112 | A | 2/1993 |
| JP | 6121797 | | 5/1994 |
| JP | 6285078 | | 10/1994 |
| JP | 6511401 | A | 12/1994 |
| JP | H06343644 | A | 12/1994 |
| JP | H07265328 | A | 10/1995 |
| JP | 8056955 | A | 3/1996 |
| JP | 080566955 | A | 5/1996 |
| JP | 08252263 | | 10/1996 |
| JP | 8289895 | A | 11/1996 |
| JP | H08289895 | | 11/1996 |
| JP | 8317934 | A | 12/1996 |
| JP | 8317936 | A | 12/1996 |
| JP | H08317934 | | 12/1996 |
| JP | H08317936 | | 12/1996 |
| JP | 910223 | A | 1/1997 |
| JP | 09000538 | | 1/1997 |
| JP | 9122138 | A | 5/1997 |
| JP | 0010000195 | | 1/1998 |
| JP | 10155798 | A | 6/1998 |
| JP | H10155798 | A | 6/1998 |
| JP | 1147149 | | 2/1999 |
| JP | H1147149 | A | 2/1999 |
| JP | H1147150 | A | 2/1999 |
| JP | H1170124 | A | 3/1999 |
| JP | H11169381 | | 6/1999 |
| JP | 2011192238 | A | 7/1999 |
| JP | H11192238 | | 7/1999 |
| JP | H11244298 | A | 9/1999 |
| JP | 2000102545 | A | 4/2000 |
| JP | 2000135222 | A | 5/2000 |
| JP | 2000342599 | A | 12/2000 |
| JP | 2000350732 | A | 12/2000 |
| JP | 2001008944 | | 1/2001 |
| JP | 2001029355 | | 2/2001 |
| JP | 2001029356 | | 2/2001 |
| JP | 2001003400 | | 4/2001 |
| JP | 2001128990 | A | 5/2001 |
| JP | 2001190564 | A | 7/2001 |
| JP | 2002136525 | A | 5/2002 |
| JP | 2002528166 | A | 9/2002 |
| JP | 2003116871 | A | 4/2003 |
| JP | 2003175052 | A | 6/2003 |
| JP | 2003245285 | A | 9/2003 |
| JP | 2004517668 | A | 6/2004 |
| JP | 2004528869 | A | 9/2004 |
| JP | 2005152663 | A | 6/2005 |
| JP | 2005253789 | A | 9/2005 |
| JP | 2006015078 | A | 1/2006 |
| JP | 2006501939 | A | 1/2006 |
| JP | 2006095316 | A | 4/2006 |
| JP | 2011070124 | A | 4/2011 |
| JP | 2011125195 | A | 6/2011 |
| JP | 2011169381 | A | 9/2011 |
| JP | H0630945 | B2 | 11/2016 |
| SU | 401367 | A1 | 11/1974 |
| WO | 9102493 | A1 | 3/1991 |
| WO | 9400059 | A1 | 1/1994 |
| WO | 0036986 | A1 | 6/2000 |
| WO | 0059392 | A1 | 10/2000 |
| WO | 0115614 | A1 | 3/2001 |
| WO | 0154604 | A1 | 8/2001 |
| WO | 0245589 | A2 | 6/2002 |
| WO | 02080799 | A1 | 10/2002 |
| WO | 2006021269 | A1 | 3/2006 |
| WO | 2005110264 | A2 | 4/2006 |
| WO | 2008040483 | A1 | 4/2008 |
| WO | 2011018154 | A1 | 2/2011 |

OTHER PUBLICATIONS

Michael Choti, "Abdominoperineal Resection with the LigaSure Vessel Sealing System and LigaSure Atlas 20 cm Open Instrument" Innovations That Work, .quadrature.Jun. 2003.

Chung et al., "Clinical Experience of Sutureless Closed Hemontoidectomy with LigaSure"; Diseases of the Colon & Rectum vol. 46, No. Jan. 1, 2003.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas MedicalCenter, Charlotte, NC; Date: Aug. 2003.

Peterson et al., "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000, 6 pages.

Johnson et al. "Evaluation of a Bipolar Electrothermal Vessel Sealing Device in Hemorrhoidectomy" Sales/Product Literature; Jan., 2004.

E. David Crawford, "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicoletomy Using the LigaSure Vessel Sealing System" Innovations That Work,. quadrature.Sep. 1999.

Kennedy et al. "High-burst-strength, feedback-controlled bipolar vessel sealing" Surgical Endoscopy (1998) 12:876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work,.quadrature. Jun. 2002.

(56) References Cited

OTHER PUBLICATIONS

Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" . Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001, 1 page.
Sayfan et al. "Sutureless Closed Hemorrhoidectomy: A New Technique" Annals of Surgery vol. 234 No. 1, Jul. 2001 pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery {2001) 71 .9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999, 1 page.
Barbara Levy, "Use of a New Vessel Ligation Device During Vaginal Hysterectomy" FIGO 2000, Washington, D.C .. (1 Page).
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue" MICCAI 2005; LNCS 3750 pp. 624-632 Dated: 2005.
McLellan et al., "Vessel Sealing for Hemostasis During Pelvic Surgery" Int'l Federation of Gynecology and Obstetrics Figo World Congress 2000, Washington, DC.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremeich.
U.S. Appl. No. 13/731,674, filed Dec. 31, 2012; inventor: Siebrecht.
Chinese office action issued in corresponding application No. 201310303960.0 dated Feb. 24, 2017.
Examination report issued in corresponding EP application No. 13177024.0 on Nov. 2, 2017.

* cited by examiner

SURGICAL FORCEPS INCLUDING REPOSABLE END EFFECTOR ASSEMBLIES

CROSS REFERENCE TO RELATED APPLICATIONS

The present application is a divisional of U.S. patent application Ser. No. 16/559,982, filed Sep. 4, 2019, which is a divisional of U.S. patent application Ser. No. 15/019,490, filed Feb. 9, 2016, now U.S. Pat. No. 10,413,353, which is a divisional of U.S. patent application Ser. No. 13/936,510, filed on Jul. 8, 2013, now U.S. Pat. No. 9,301,798, which claims the benefit of and priority to U.S. Provisional Application Ser. No. 61/673,308, filed on Jul. 19, 2012, the entire contents of each of which are hereby incorporated herein by reference.

BACKGROUND

Technical Field

The present disclosure relates generally to the field of reposable or reusable surgical instruments. In particular, the present disclosure relates to instruments having separable and replaceable components to provide clean, sterile, or refurbished surfaces in each instance of use.

Background of Related Art

Instruments such as electrosurgical forceps are commonly used in open and endoscopic surgical procedures to coagulate, cauterize, and/or seal tissue. Such forceps typically include a pair of jaw members that can be controlled by a surgeon to grasp targeted tissue therebetween. More specifically, the jaw members may be approximated relative to one another to apply a mechanical clamping force to tissue, while electrosurgical energy is delivered to tissue via one or more electrode surfaces of the jaw members. The combination of mechanical clamping force and electrosurgical energy delivery has been demonstrated to seal adjacent layers of tissue captured between the jaw members. Thereafter, the sealed tissue may be transected by advancing a knife between the jaw members.

During use, various tissue-contacting components of an electrosurgical forceps (and other similar instruments) may become contaminated or degraded. For example, electrodes may become contaminated as portions of treated tissue adhere to the tissue-contacting surfaces of the electrodes. Also, the knife may become dull and less effective in transecting tissue after repeated use, even in a single surgical procedure. In order to provide clean electrodes and a sharp knife for a particular surgical procedure, a brand new instrument is often used. Once the procedure is complete, the used instrument is discarded. Instruments that are reposable, or reusable for multiple procedures, or instruments incorporating reposable components, on the other hand, reduce waste and instrumentation costs per procedure by permitting the reuse of one or more components thereof.

SUMMARY

As used herein, as is traditional, the term "proximal" refers to the end of the apparatus, or portion thereof, which is closer to the user and the term distal refers to the end of the apparatus, or portion thereof, which is further from the user. To the extent consistent, any of the aspects described herein may be used in conjunction with any of the other aspects described herein.

A surgical forceps provided in accordance with aspects of the present disclosure includes a housing including a movable handle coupled thereto. The movable handle is movable between an initial position and a compressed position. A drive bar is operably coupled to the movable handle at a proximal end of the drive bar such that movement of the movable handle between the initial position and the compressed position effects longitudinal translation of the drive bar. The drive bar further includes one or more coupling members disposed at a distal end thereof. An end effector assembly includes first and second jaw members. One or both of the jaw members is movable relative to the other between a spaced-apart position and an approximated position for grasping tissue therebetween. Each jaw member defines a cam slot. A cam pin is slidably disposed within the cam slot of each of the first and second jaw members. The coupling member(s) of the drive bar is configured to releasably engage the cam pin such that movement of the movable handle between the initial position and the compressed position effects movement of the jaw members between the spaced-apart position and the approximated position.

In one aspect, the coupling member includes a pair of resilient fingers configured for releasable snap-fit engagement about the cam pin.

In another aspect, a shaft is disposed about the drive bar and extends between the housing and the end effector assembly. The shaft is configured to releasably engage the end effector assembly at a distal end of the shaft.

In yet another aspect, the first and second jaw members are pivotably coupled to one another about a pivot pin. The pivot pin is releasably engagable with the shaft to releasably engage the end effector assembly and shaft to one another.

In still another aspect, the end effector assembly further includes a connector. The first and second jaw members are pivotably coupled to the connector and the connector, in turn, is releasably engagable with the shaft.

In another aspect, the connector includes a pair of cam slots defined therethrough. The cam slots are configured to slidably engage the cam pin therein.

In still yet another aspect, the housing further includes a trigger coupled thereto. The trigger is operably coupled to a knife drive sleeve extending distally from the housing. The trigger is movable between an un-actuated position and an actuated position to effect longitudinal translation of the knife drive sleeve. In such aspects, the end effector assembly further includes a knife movable between a retracted position and an extended position to cut tissue grasped therebetween. The knife includes one or more engagement members disposed at a proximal end thereof that are configured to releasably engage the knife drive sleeve such that movement of the trigger between the un-actuated position and the actuated position effects movement of the knife between the retracted position and the extended position.

Another surgical forceps provided in accordance with aspects of the present disclosure includes a housing including a movable handle coupled thereto that is movable between an initial position and a compressed position. A shaft extends distally from the housing and includes a pivot pin mounted at a distal end thereof. A drive bar is slidably disposed within the shaft and is operably coupled to the movable handle at a proximal end of the drive bar such that movement of the movable handle between the initial position and the compressed position effects longitudinal translation of the drive bar. The drive bar further includes a cam pin mounted at a distal end thereof. An end effector assembly includes first and second jaw members movable relative to one another between a spaced-apart position and an approximated position for grasping tissue therebetween. Each jaw member includes a distal jaw portion and a proximal flange. The proximal flanges of the jaw members each define a pivot aperture and a cam slot therethrough. Each of the pivot apertures is configured to releasably engage the pivot pin therein to pivotably engage the end effector assembly at the distal end of the shaft and each of the cam slots is configured to releasably engage the cam pin therein to operably engage the end effector assembly to the drive bar such that movement of the movable handle between the initial position and the compressed position effects movement of the jaw members between the spaced-apart position and the approximated position.

In one aspect, each of the proximal flanges of the jaw members includes a first mouth providing access to the pivot aperture thereof and a second mouth providing access to the cam slot thereof. In such aspects, the pivot pin is configured to pass through the first mouth of each of the proximal flanges and into the pivot aperture thereof to releasably engage the jaw members to the shaft and the cam pin is configured to pass through the second mouth of each of the proximal flanges and into the cam slot thereof to releasably engage the jaw members to the drive bar.

In another aspect, the pivot pin includes first and second spring-loaded pivot pins configured to releasable engage one of the pivot apertures of the jaw members. Alternatively or additionally, the cam pin may include first and second spring-loaded cam pins slidably disposed within cam slots defined within the shaft and configured for releasable engagement within one of the cam slots of the jaw members.

In still another aspect, the pivot pin includes first and second pivot pins each including a snap-fit feature disposed at a free end thereof. The pivot pins are configured to releasably, snap-fittingly engage one of the pivot apertures of the jaw members. Likewise, the cam pin may include first and second cam pins slidably disposed within cam slots defined within the shaft. Each cam pin includes a snap-fit feature disposed at a free end thereof such that each cam pin can releasably, snap-fittingly engage one of the cam slots of the jaw members.

A forceps provided in accordance with other aspects of the present disclosure includes a housing having a movable handle coupled thereto and movable between an initial position and a compressed position. A shaft extends distally from the housing and drive bar is slidably disposed within the shaft. The drive bar is operably coupled to the movable handle at a proximal end of the drive bar such that movement of the movable handle between the initial position and the compressed position effects longitudinal translation of the drive bar. One of the shaft and the drive bar includes a first electrically-conductive segment adapted to connect to a positive terminal of an energy source and a second electrically-conductive segment adapted to connect to a negative terminal of an energy source. An end effector assembly includes first and second jaw members. A portion of each of the jaw members is formed from an electrically-conductive material and the first and second jaw members are electrically insulated from one another. The jaw members are movable relative to one another between a spaced-apart position and an approximated position for grasping tissue therebetween. The jaw members are pivotably coupled to the shaft via a pivot pin and are operably coupled to the drive bar via a cam pin such that longitudinal translation of the drive bar moves the jaw members between the spaced-apart and approximated positions. One of the drive pin and the cam pin includes a first electrically-conductive portion and a second electrically-conductive portion that is electrically insulated from the first electrically-conductive portion. The first electrically-conductive portion is configured to electrically couple the first electrically-conductive segment to the first jaw member and the second electrically-conductive portion is configured to electrically couple the second electrically-conductive segment to the second jaw member. Thus, the first and second jaw members may conduct energy therebetween and through tissue grasped therebetween to treat tissue.

In one aspect, the pin includes the first electrically-conductive portion disposed at a first end thereof, the second electrically-conductive portion disposed at a second end thereof, and an electrically-insulative portion disposed therebetween. Alternatively, the pin may include an electrically-insulative body having first and second spaced-apart electrically-conductive sleeves disposed thereabout.

In another aspect, the end effector assembly is releasably engagable with the shaft and the drive bar.

BRIEF DESCRIPTION OF THE DRAWINGS

Various aspects of the present disclosure are described herein with reference to the drawings wherein like reference numerals identify similar or identical elements.

DETAILED DESCRIPTION

The operating features and inter-cooperating components of surgical instruments provided in accordance with the present disclosure are shown in the Figures and described hereinbelow. More specifically, the surgical instruments are shown as forceps, e.g., forceps 10 (FIG. 1), although the present disclosure is equally applicable for use with any other suitable surgical instrument having a handle assembly operable to control and/or manipulate an end effector assembly that is releasably engagable therewith. Obviously, different connections and considerations apply to each particular type of instrument; however, the novel aspects with respect to the releasable engagement of the end effector assembly and the surgical instrument remain generally consistent regardless of the particular type of instrument used. For the purposes herein, forceps 10 is generally described.

Figure 1:
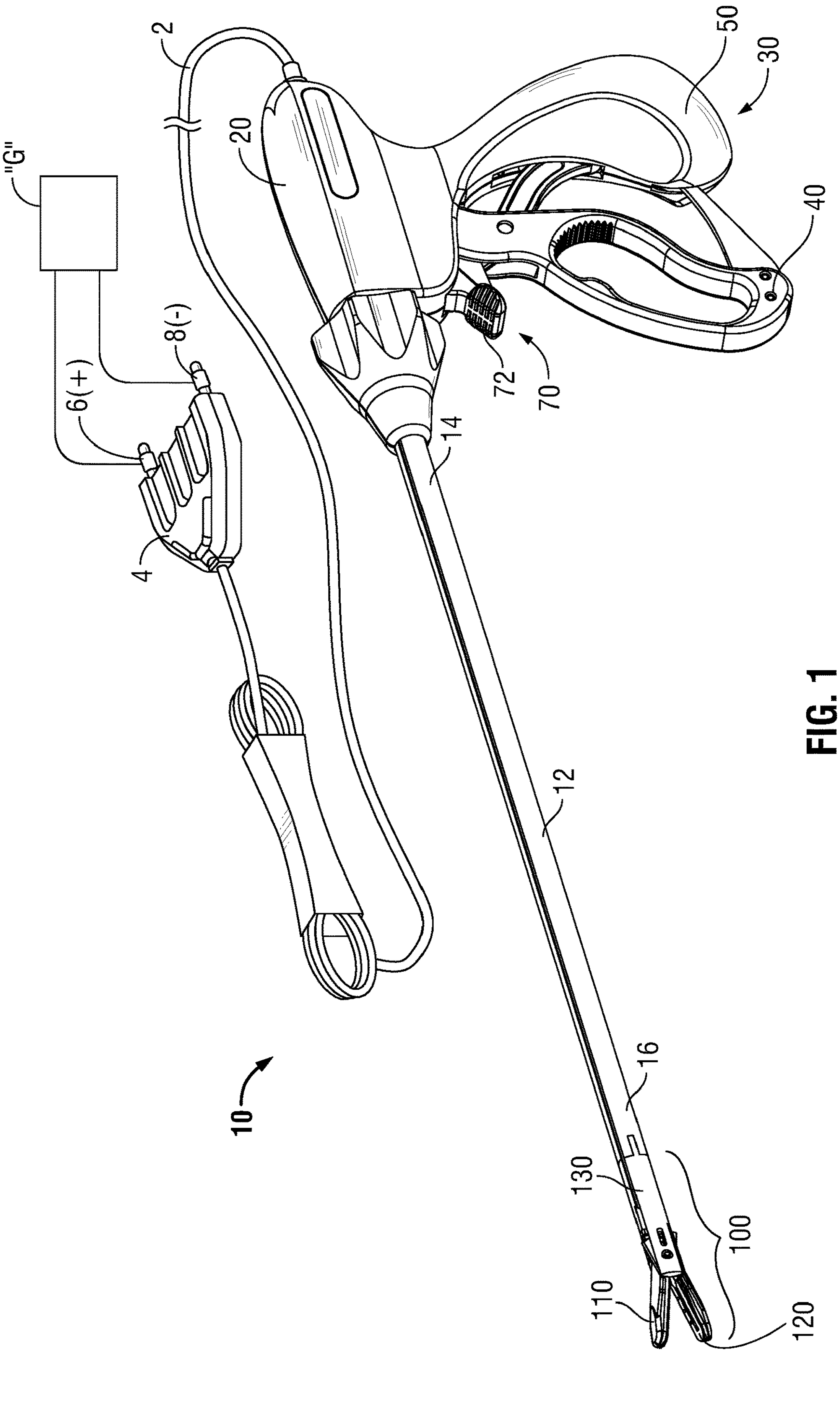
FIG. 1 is a perspective view of an endoscopic surgical forceps provided in accordance with the present disclosure.

Referring to FIG. 1, forceps 10 is shown generally including a housing 20, a handle assembly 30, a trigger assembly 70, and an end effector assembly 100 that mutually cooperate to grasp, treat, and divide tubular vessels and vascular tissues. Forceps 10 further includes a shaft 12 having a distal end 16 configured to releasably engage end effector assembly 100 and a proximal end 14 configured to mechanically engage housing 20.

A cable 2 extends between housing 20 of forceps 10 and an energy source, e.g., generator "G," and includes a connector 4 for coupling forceps 10 to generator "G." Alternatively, forceps 10 may be configured as a handheld device incorporating a generator (not shown) and battery (not shown) within housing 20. Connector 4 includes two prong members 6, 8 that are dimensioned to mechanically and electrically connect forceps 10 to opposite terminals, e.g., positive or active (+) and negative or return (−) terminals associated with generator "G." Thus, bipolar electrosurgical energy may be provided to forceps 10 for application to tissue, although forceps 10 and generator "G" may additionally or alternatively be configured for delivering monopolar electrosurgical energy to tissue, or may be configured to deliver any other suitable form of energy, e.g., ultrasonic energy, microwave energy, thermal energy, light energy, etc., to tissue. In a monopolar configuration, forceps 10 delivers electrosurgical energy from an active terminal, e.g. (+), while a return pad (not shown) is remotely placed on the patient to provide a return path to the opposite terminal, e.g. (−), of generator "G."

With continued reference to FIG. 1, handle assembly 30 includes a fixed handle 50 and a movable handle 40. Fixed handle 50 is integrally associated with housing 20 and movable handle 40 is movable relative to fixed handle 50 between an initial position and a compressed position to impart movement of jaw members 110 and 120 of end effector assembly 100 between a spaced-apart position and an approximated position for grasping tissue therebetween. More specifically, movable handle 40 is operably coupled, within housing 20, to a drive bar 140 (FIG. 3) that extends through shaft 12, ultimately coupling to end effector assembly 100 such that compression of movable handle 40 relative to fixed handle 50 translates drive bar 140 (FIG. 3) relative to end effector assembly 100, thereby pivoting jaw members 110, 120 relative to one another from the spaced-apart position to the approximated position and such that release or return of movable handle 40 to the initial position translates drive bar 140 (FIG. 3) in the opposite direction thereby pivoting jaw members 110, 120 relative to one another from the approximated position back to the spaced-apart position.

Trigger 72 of trigger assembly 70 is selectively actuatable to deploy a knife 190 (FIG. 2) from shaft 12 to between jaw members 110, 120 to cut tissue grasped therebetween. More specifically, trigger 72 is operably coupled, within housing 20, to a knife drive sleeve 180 (FIG. 2) that extends through shaft 12, ultimately coupling to knife 190 (FIG. 2) of end effector assembly 100 such that, upon actuation of trigger 72, knife 190 (FIG. 2) is translated from a retracted position, wherein knife 190 (FIG. 2) is positioned proximally of jaw members 110, 120, to an extended position, wherein knife 190 (FIG. 2) extends at least partially between jaw members 110, 120 to cut tissue grasped therebetween.

Various end effector assemblies, or components thereof, configured to releasably engage distal end 16 of shaft 12 of forceps 10 (or any other suitable surgical instrument) are described below with reference to FIGS. 2-9. As can be appreciated, in order to operably engage an end effector assembly to forceps 10 at distal end 16 of shaft 12, the end effector assembly must be operably coupled to the drive mechanism of forceps 10 and, in embodiments where a knife assembly is provided, must be operably coupled to the knife mechanism of forceps 10 such that manipulation of movable handle 40 and manipulation of trigger 72 effect opening and closing of the jaw members of the end effector assembly and extension and retraction of the knife of the end effector assembly, respectively. Further, any of the features of the end effector assemblies and components thereof provided herein, to the extent consistent, may be used similarly in conjunction with any of the other end effector assemblies and components thereof provided herein.

The end effector assemblies described hereinbelow and/or the components thereof, e.g., the jaw members and knife, may be configured as disposable components configured to be discarded and replaced after a single use (or a single procedure), while the remaining components of forceps 10 may be formed from a sterilizable material such that they may be sterilized, e.g., placed in an autoclave (not shown), after each procedure for repeat use in conjunction with subsequent (or re-sterilized) end effector assemblies or components thereof. The end effector assemblies or components thereof, however, may be alternatively sterilizable for reuse. In such embodiments, the reposability of the end effector assemblies or components thereof facilitates the sterilization of these components. Further, the remaining components of forceps 10, or components thereof, may alternatively be configured as disposable, rather than reusable, components. Regardless of the configuration, e.g., regardless of which components are reusable or disposable, reposable end effector assemblies are advantageous in that the surgeon may select the end effector assembly or particular components thereof for use with forceps 10 that is best suited for the particular procedure to be performed, i.e., the surgeon may customize forceps 10 to the particular procedure to be performed by selecting a particular end effector assembly or component thereof without requiring an entirely new surgical instrument. As can be appreciated, requiring only a new end effector assembly or component thereof for each use, rather than an entire new surgical instrument, helps reduce the equipment costs associated with performing a particular surgical procedure. Likewise, the ability to interchangeably use different end effector assemblies or components thereof allows a single instrument to be customizable for use in various different procedures, rather than requiring a different instrument for each different procedure.

Figure 2:
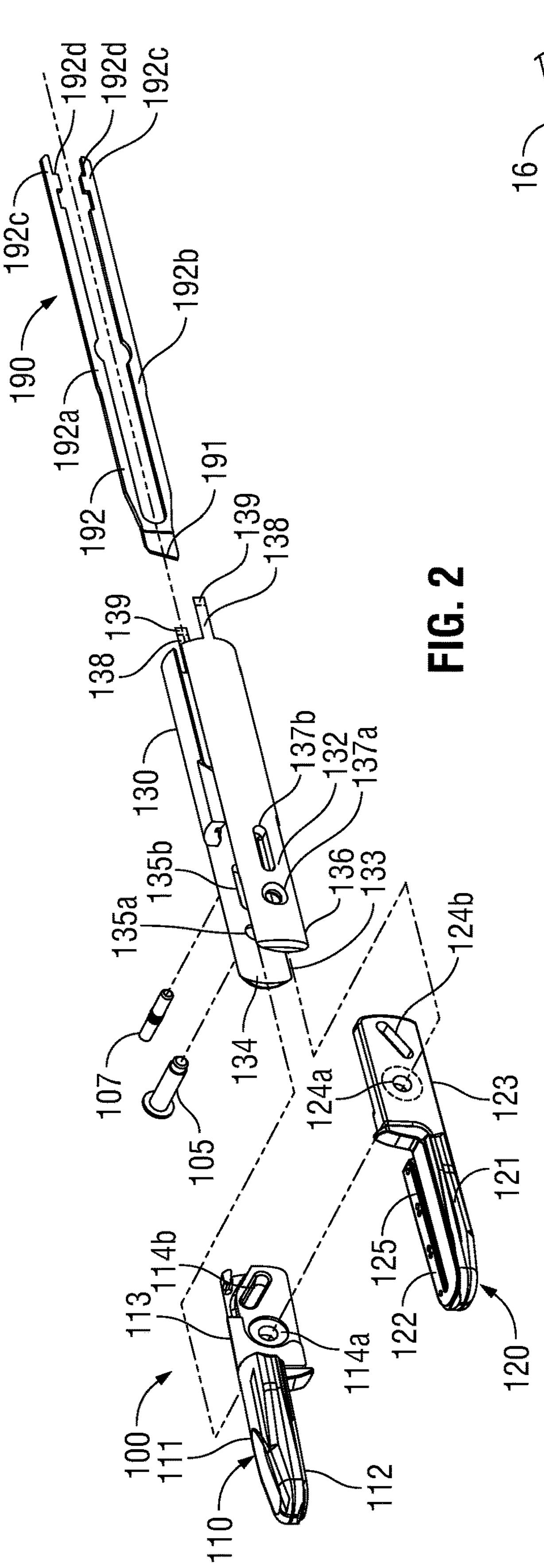
FIG. 2 is a perspective view of an end effector assembly configured for use with the forceps of FIG. 1 and shown with parts separated.
Figure 3:
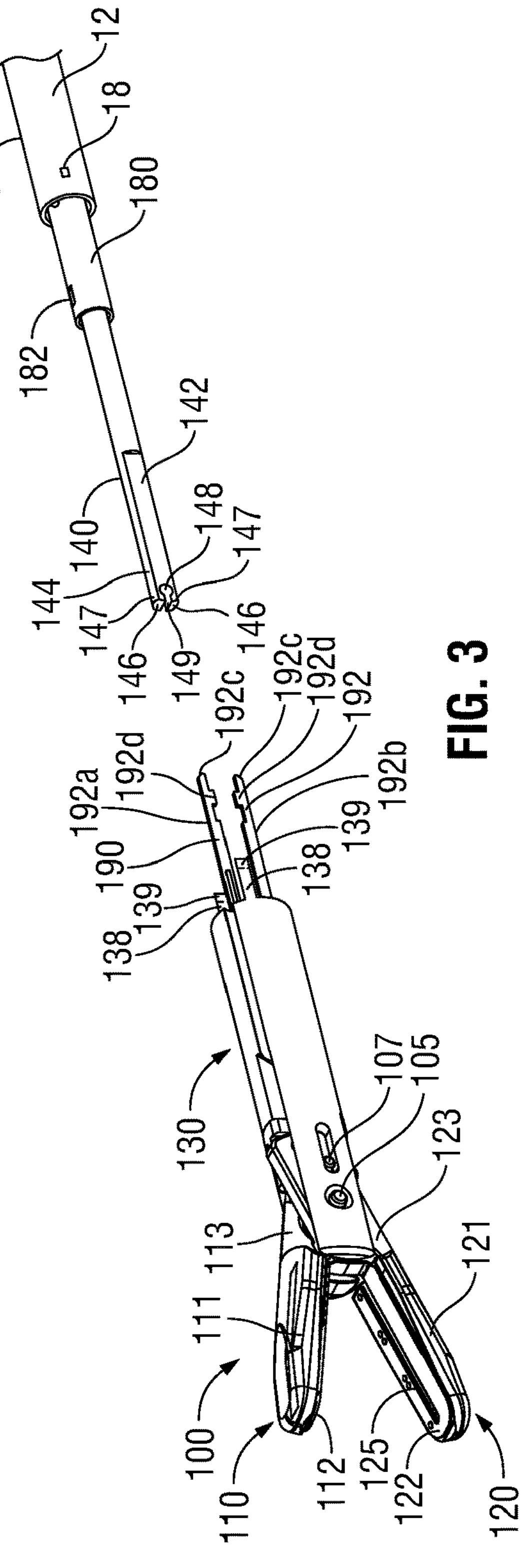
FIG. 3 is a perspective view of the end effector assembly of FIG. 2 shown disengaged from the forceps of FIG. 1.

Turning now to FIGS. 2-3, one embodiment of an end effector assembly 100 configured for releasable engagement with forceps 10 is shown including a pair of jaw members 110 and 120 and a longitudinal connector 130. End effector assembly 100 is designed as a bilateral assembly, i.e., both jaw members 110 and 120 are movable relative to one another and to connector 130 about a pivot pin 105, although end effector assembly 100 may alternatively be configured as a unilateral end effector assembly. Each jaw member 110, 120 of end effector assembly 100 includes a distal jaw portion 111, 121 that supports an electrically-conductive tissue sealing plate 112, 122, respectively, thereon, and a proximal flange 113, 123 extending distally from the respective distal jaw portion 111, 121 for operably mounting jaw members 110, 120, respectively, to connector 130. Either or both electrically-conductive tissue sealing plates 112, 122 are adapted to connect to a source of energy, e.g., generator "G," for conducting energy therebetween and through tissue grasped between jaw members 110, 120 to treat, e.g., seal, tissue. Tissue sealing plates 112, 122 and distal jaw portions 111, 121 of one or both of jaw members 110, 120, respectively, may cooperate to define a longitudinally-oriented knife channel 125 therein that is configured to permit reciprocation of knife 190 therethrough to cut tissue grasped between jaw members 110, 120. Proximal flanges 113, 123 of jaw members 110, 120, respectively, each include a pivot aperture 114*a*, 124*a*, respectively, defined therethrough that is configured to receive pivot pin 105, and an oppositely-angled cam slot 114*b*, 124*b*, respectively, defined therethrough that is configured to receive cam pin 107.

Connector 130 defines a generally longitudinal shaft-like configuration dimensioned similar to shaft 12 and having a bifurcated distal portion 132 including first and second flanges 134, 136, respectively, that define a channel 133 therebetween for receiving jaw members 110 and 120. Each flange 134, 136 defines a pivot aperture 135*a* and 137*a*, respectively, therethrough for receipt of pivot pin 105, and a longitudinal cam slot 135*b*, 137*b*, respectively, configured to receive cam pin 107. Connector 130 further includes one or more engagement tabs 138 extending proximally from the proximal end thereof that each include an engagement protrusion 139 extending inwardly therefrom at the free end thereof. Engagement protrusions 139 of engagement tabs 138 are configured for releasable engagement with complementary engagement apertures 18 defined within shaft 12 towards distal end 16 thereof to releasably engage connector 130 to distal end 16 of shaft 12. Other releasable engagement mechanisms, e.g., friction-fit, snap-fit, threaded-engagement, etc., for releasably engaging connector 130 and shaft 12 to one another are also contemplated.

As mentioned above, movable handle 40 (FIG. 1) of forceps 10 (FIG. 1) is operably coupled to drive bar 140. Drive bar 140 extends through shaft 12 and includes a distal end 142 configured to releasably engage cam pin 107, which is positioned within, or is configured for positioning within cam slots 114*b*, 124*b* and 135*b*, 137*b* of jaw members 110, 120 and flanges 134, 136 of connector 130, respectively. More specifically, drive bar 140 includes a coupling member 144 disposed at distal end 142 thereof. Coupling member 144 includes two spaced-apart, arcuate fingers 146 that cooperate to define a generally transverse, cylindrical aperture 148 therebetween. Free ends 147 of fingers 146 define an opening 149 therebetween in communication with aperture 148. Fingers 146 are resiliently flexible relative to one another between a normal configuration, wherein free ends 147 of fingers 146 are relatively closer-together such that opening 149 defines a minimum dimension, and a flexed configuration, wherein free ends 147 of fingers 146 are relatively further spaced-apart such that opening 149 defines a maximum dimension. In the normal configuration, fingers 146 are spaced a distance less than a cross-sectional dimension of cam pin 107, thus inhibiting insertion of cam pin 107 into or withdrawal of cam pin 107 from aperture 148. However, when cam pin 107 is urged with sufficient force into free ends 147 of fingers 146, fingers 146 are temporarily deflected, or flexed apart from one another towards the flexed configuration to permit passage of cam pin 107 through opening 149 and into/out of aperture 148. Upon achieving the engaged position, wherein cam pin 107 is disposed within aperture 148, fingers 146 are permitted to return, e.g., snap-back, to the normal configuration, thus retaining cam pin 107 within aperture 107. That is, aperture 148 is sufficiently dimensioned so as to accommodate cam pin 107 therein while fingers 146 are disposed in the normal configuration.

With continued reference to FIGS. 2-3, as mentioned above, end effector assembly 100 further includes a knife 190 that is selectively translatable between the retracted position and the extended position to cut tissue grasped between jaw members 110, 120. More specifically, knife 190 of end effector assembly 100 includes a distal blade 191 configured to facilitate cutting tissue upon translation of knife 190 between jaw members 110, 120, and an elongated body portion 192. Body portion 192 of knife 190 is bifurcated to define first and second arms 192*a*, 192*b*, each arm 192*a*, 192*b* having an engagement protrusion 192*d* disposed towards the free end 192*c* thereof and extending inwardly therefrom. Arms 192*a*, 192*b* are configured to resiliently flex upon approximation of body portion 192 of knife 190 with knife drive sleeve 180 such that engagement protrusions 192*d* can engage complementary engagement recesses 182 of knife drive sleeve 180 to operably couple knife 190 and knife drive sleeve 180 to one another. The bifurcated configuration of knife 190 also permits translation of knife 190 about pivot pin 105 and cam pin 107, thus permitting knife 190 to translate between the retracted and extended positions upon actuation of trigger 72 of trigger assembly 70.

End effector assembly 100 may be provided in a fully assembled condition (as shown in FIG. 3) such that the user need only engage end effector assembly 100 to forceps 10 (as will be described below) in preparation for use. In such pre-assembled embodiments, jaw members 110, 120, during manufacturing, are engaged to connector 130 via the disposition of pivot pin 105 through pivot aperture 135*a* of flange 134 of connector 130, pivot aperture 114*a* of proximal flange 113 of jaw member 110, pivot aperture 124*a* of proximal flange 123 of jaw member 120, and pivot aperture 137*a* of flange 136 of connector 130. Likewise, during manufacturing, cam pin 107 is slidably engaged within cam slot 135*b* of flange 134 of connector 130, cam slot 114*b* of proximal flange 113 of jaw member 110, cam slot 124*b* of proximal flange 123 of jaw member 120, and cam slot 137*b* of flange 136 of connector 130. Further, during manufacturing, knife 190 may be slidably positioned about pivot pin 105 and cam pin 107, as shown in FIG. 3. Alternatively, jaw members 110, 120 may be pre-assembled to connector 130, while knife 190 is not pre-assembled, thus allowing the user to select a desired knife 190, e.g., a desired size, shape and/or configuration, for use with end effector assembly 100, depending on a particular purpose.

Alternatively, end effector assembly 100 may be assembled manually by the user. With reference to FIGS. 2-3, for user-assembly of end effector assembly 100, the user aligns pivot aperture 114*a* of proximal flange 113 of jaw member 110, pivot aperture 124*a* of proximal flange 123 of jaw member 120, and pivot aperture 137*a* of flange 136 of connector 130 and inserts pivot pin 105 through the aligned apertures 135*a*, 114*a*, 124*a*, 137*a* to pivotably engage jaw members 110, 120 at the distal end of connector 130. An end cap (not shown) or other suitable mechanism for retaining pivot pin 105 in engagement within apertures 135*a*, 114*a*, 124*a*, 137*a* may also be provided. With jaw members 110, 120 pivotably engaged at the distal end of connector 130 (or prior thereto), the user advances cam pin 107 through cam slot 135*b* of flange 134 of connector 130, cam slot 114*b* of proximal flange 113 of jaw member 110, cam slot 124*b* of proximal flange 123 of jaw member 120, and cam slot 137*b* of flange 136 of connector 130 to slidably and pivotable engage cam pin 107 therein. Similarly as with pivot pin 105, end caps (not shown), or any other suitable mechanism may be provided to retain cam pin 107 in slidable engagement within slots 135*b*, 114*b*, 124*b*, 137*b*. Next, knife 190 is inserted about pivot pin 105 and cam pin 107 to the retracted position, as shown in FIG. 3. In these unassembled embodiments, as can be appreciated, the user may select particular components to be used, depending on a particular purpose. For example, jaw members of different sizes or configurations may be selectively chosen and assembled in accordance with the particular procedure to be performed, anatomical considerations of the patient, and/or other factors.

With reference to FIGS. 1-3, the engagement and use of forceps 10 and end effector assembly 100 is described. Initially, in preparation for use, in embodiments where end effector assembly 100 is not pre-assembled, or is only partially pre-assembled, end effector assembly 100 is assembled, as described above. Once end effector assembly 100 has been assembled, it can be engaged to forceps 10.

In order to engage end effector assembly 100 to forceps 10, connector 130 is aligned with and approximated relative to distal end 16 of shaft 12. As connector 130 is approximated relative to shaft 12, engagement tabs 138 of connector 130 are flexed outwardly about the outer periphery of shaft 12 until engagement protrusions 139 "snap" into engagement complementary engagement apertures 18 defined within shaft 12, thus allowing engagement tabs 138 to return to their neutral position. This engagement between engagement protrusions 138 and engagement recesses 18 securely engages connector 130 of end effector assembly 100 and shaft 12 to one another.

Simultaneously or near-simultaneously with the engagement of connector 130 and shaft 12, cam pin 107 is approximated relative to coupling member 144 of drive bar 140. Eventually, upon further approximation, cam pin 107 is urged into fingers 146 of coupling member 144 such that fingers 146 are flexed apart from one another towards the flexed configuration to permit passage of cam pin 107 through opening 149 and into aperture 148. Once cam pin 107 is disposed within aperture 148, as mentioned above, fingers 146 are returned under bias return to their normal configurations to retain cam pin 107 therein. With cam pin 107 engaged within aperture 148 of coupling member 144 of drive bar 140, jaw members 110, 120 are operably coupled to handle assembly 30, thus allowing manipulation of movable handle 40 to effect opening or closing of jaw members 110, 120, as will be described in greater detail below.

Simultaneously or near-simultaneously with the engagement of connector 130 and shaft 12 and/or the engagement of cam pin 107 and drive bar 140, knife 190 is approximated relative to knife drive sleeve 180. Eventually, upon further approximation, arms 192*a*, 192*b* of knife body 192 are flexed about knife drive sleeve 180 and are translated therealong until engagement protrusions 192*d* of knife 190 engage complementary engagement recesses 182 of knife drive sleeve 180 to operably couple knife 190 and knife drive sleeve 180 to one another. With knife 190 engaged to knife drive sleeve 180, trigger 72 of trigger assembly 70 may be selectively actuated to translate knife 190 between the retracted and extended positions for cutting tissue grasped between jaw members 110, 120.

With forceps 10 fully assembled, as described above, forceps 10 is ready for use. In use, initially, with jaw members 110, 120 disposed in the spaced-apart position, forceps 10 is manipulated and/or maneuvered into position such that tissue to be grasped, treated, and/or divided in disposed between jaw members 110, 120. At this point, movable handle 40 is disposed in the initial position (such that jaw members 110, 120 remain in the spaced-apart position) and trigger 72 is disposed in the un-actuated position (such that knife 190 is disposed in the retracted position).

In order to grasp tissue between jaw members 110, 120, movable handle 40 is compressed, or pulled proximally relative to fixed handle 50 from the initial position towards the compressed position such drive bar 140 is translated proximally. Proximal translation of drive bar 140 likewise pulls cam pin 107 (due to the engagement of coupling member 144 about cam pin 107) to translate proximally through slots 136*b*, 114*b*, 124*b*, 137*b*, thereby pivoting jaw members 110, 120 relative to one another and about pivot pin 105 towards the approximated position to grasp tissue therebetween.

With jaw members 110, 120 in the approximated position grasping tissue therebetween, tissue sealing plate 112 and/or tissue sealing plate 122 may be energized to conduct energy between tissue sealing plates 112, 122 and through tissue to treat, e.g., seal, tissue. At the completion of tissue treatment, or where it is only desired to cut tissue, trigger 72 of trigger assembly 70 may be actuated to translate knife drive sleeve 180 distally, thereby translating knife 190 distally (due to the coupling of knife 190 to knife drive sleeve 180) between jaw members 110, 120 and through knife channel(s) 125 to cut tissue grasped between jaw members 110, 120.

Once the desired grasping, treating, and/or cutting of tissue is complete, movable handle 40 may be returned to the initial position, thereby urging drive bar 140 and cam pin 107 distally such that jaw members 110, 120 are returned to the spaced-apart position to release tissue. Thereafter, the above-described use may be repeated to treat and/or cut additional tissue, or end effector assembly 100 may be disengaged from shaft 12 of forceps 10. In order to disengage end effector assembly 100 from forceps 10, connector 130 is moved apart from shaft 12 with sufficient urging so as to disengage engagement protrusions 138 from engagement recesses 18, thereby disengaging connector 130 of end effector assembly 100 and shaft 12 from one another; to disengage cam pin 107 from coupling member 144 of drive bar 140; and to disengage engagement protrusions 192*d* of arms 192*a*, 192*b* of knife 190 from engagement recesses 182 of knife drive sleeve 180, thereby fully disengaging end effector assembly 100 from forceps 10. With end effector assembly 100 fully disengaged, end effector assembly 100 (or any of the components thereof) and/or forceps 10 may be discarded or sterilized for reuse.

Figure 4A:
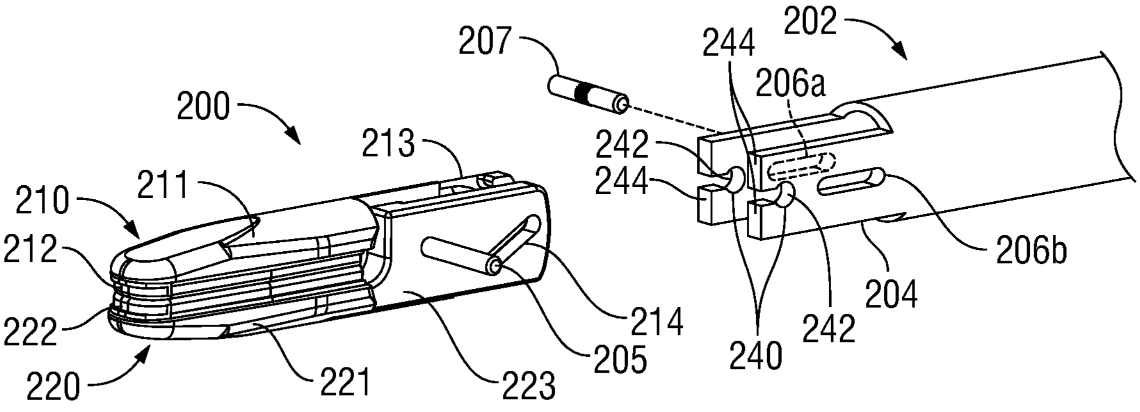
FIG. 4A is a perspective view of another end effector assembly configured for use with the forceps of FIG. 1.

Turning now to FIG. 4A, another embodiment of an end effector assembly 200 configured for releasably engagement with a shaft 202 of a forceps, e.g., forceps 10 (FIG. 1), or any other suitable surgical instrument is shown including first and second jaw members 210, 220, respectively, preassembled together as a unit. End effector assembly 200 is similar to end effector assembly 100 (FIGS. 1-3) and, thus, only the differences therebetween will be described in detail below, while similarities will only be summarily described or omitted entirely.

First and second jaw members 210, 220 of end effector assembly 200 each include a distal jaw portion 211, 221 that supports an electrically-conductive tissue sealing plate 212, 222, respectively, thereon, and a proximal flange 213, 223 extending distally from the respective distal jaw portion 211, 221. However, different from end effector assembly 100 (FIGS. 1-3), end effector assembly 200 does not include a connector but, rather, jaw members 210, 220 are directly engagable with shaft 202. More specifically, pivot pin 205 is formed from first and second halves that are fixedly mounted to or integrally formed with proximal flanges 213, 223 of respective jaw members 210, 220. Each pivot pin half of pivot pin 205 protrudes outwardly from the exterior surface of the respective proximal flanges 213, 223 of jaw members 210, 220. Proximal flanges 213, 223 are configured to be received within a bifurcated distal end 204 of shaft 202, e.g., the shaft of a forceps similar to forceps 10 (FIG. 1). Bifurcated distal end 204 of shaft 202 defines a pair of coupling members 240, each including an aperture 242 at the distal end thereof that is defined by a pair of fingers 244. Fingers 244 are configured to flex to permit passage of the halves of pivot pin 205 therebetween and into aperture 242 to releasably engage pivot pin 205 therein, similarly as described above with respect to the engagement of cam pin 207 and coupling member 144 of end effector assembly 100 and drive bar 140, respectively, of forceps 10 (see FIG. 2).

Proximal flanges 213, 223 of jaw members 210, 220, respectively, each further include an oppositely-angled cam slot 214 defined therethrough and configured to slidably receive a cam pin 207 therein, while bifurcated distal end 204 of shaft 202 defines a pair of longitudinal cam slots 206*a*, 206*b* on either side thereof similarly for receiving cam pin 207.

To releasably engage end effector assembly 200 to distal end 204 of shaft 202, each half of pivot pin 205 of end effector assembly 200 is snap-fit into one of the apertures 242 of coupling members 240 of bifurcated distal end 204 of shaft 202 by applying a sufficient urging force thereto, similarly as described above. The pivotably engagement of the halves of pivot pin 205 within apertures 242 of shaft 202 pivotably engages jaw members 210, 220 at distal end of shaft 202, with proximal flanges 213, 223 of jaw members 210, 220, respectively, disposed between the bifurcated distal end 204 of shaft 202. Next, cam pin 207 is advanced through and is slidably engaged within longitudinal cam slot 206*a* on one side of bifurcated distal end 204 of shaft 202, the angled cam slot (not shown) of proximal flange 213 of jaw member 210, angled cam slot 214 of proximal flange 223 of jaw member 220, and longitudinal cam slot 206*b* on the other side of bifurcated distal end 204 of shaft 202.

Once jaw members 210, 220 are pivotably engaged about distal end 204 of shaft 202 and once cam pin 207 is slidably engaged within cam slots 206*a*, 214, 206*b*, drive bar 140 (FIG. 2) may be engaged to cam pin 207 similarly as described above, e.g., via approximating drive bar 140 (FIG. 2) relative to cam pin 207 with sufficient urging so as to "snap" cam pin 207 into engagement therewith. In embodiments where a knife 190 (FIG. 2) is provided, knife 190 may be engaged to knife drive sleeve 180 (FIG. 3) similarly as described above. In this fully engaged condition, with additional reference to FIG. 1, movable handle 40 may be manipulated to effect opening or closing of jaw members 210, 220 and/or trigger 72 of trigger assembly 70 may be selectively actuated to translate knife 190 (FIG. 3) between the retracted and extended positions for cutting tissue grasped between jaw members 210, 220.

Figure 4B:
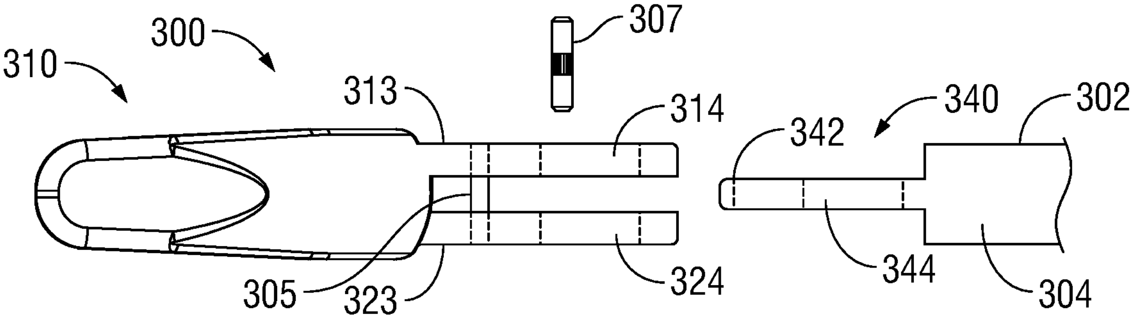
FIG. 4B is a top view of another end effector assembly configured for use with the forceps of FIG. 1.

FIG. 4B illustrates another embodiment of an end effector assembly 300 similar to end effector assembly 200 (FIG. 4A) except that pivot pin 305 extends between proximal flanges 313, 323 of jaw members 310 of end effector assembly 300, rather than half of the pivot pin extending outwardly from each flange. End effector assembly 300 further differs from end effector assembly 200 (FIG. 4A) in that proximal flanges 313, 323 are configured for positioning on either side of central distal member 340, which extends from distal end 304 of shaft 302, rather than proximal flanges 313, 323 being positionable between a bifurcated distal end of the shaft.

To releasably engage end effector assembly 300 to distal end 304 of shaft 302, end effector assembly 300 is approximated relative to central distal member 340 of shaft 302 eventually such that proximal flanges 313, 323 of jaw members 310 are disposed on either side of central distal member 340 and such that coupling member 342 of central distal member 340 engages pivot pin 305, which is disposed between proximal flanges 313, 323 of jaw members 310 of end effector assembly 300. Next, cam pin 307 is advanced through and is slidably engaged within angled cam slot 314 of proximal flange 313, longitudinal cam slot 344 of central distal member 342, and angled cam slot 324 of proximal flange 323. Thereafter, drive bar 140 (FIG. 2) may be engaged to cam pin 307, as described above, and, in embodiments where a knife 190 (FIG. 2) is provided, knife 190 (FIG. 2) may be engaged to knife drive sleeve 180 (FIG. 3), as described above. As such, with additional reference to FIG. 1, movable handle 40 may be manipulated to effect opening or closing of jaw members 310 and trigger 72 of trigger assembly 70 may be selectively actuated to translate knife 190 (FIG. 2) between the retracted and extended positions for cutting tissue grasped between jaw members 310.

Figure 5:
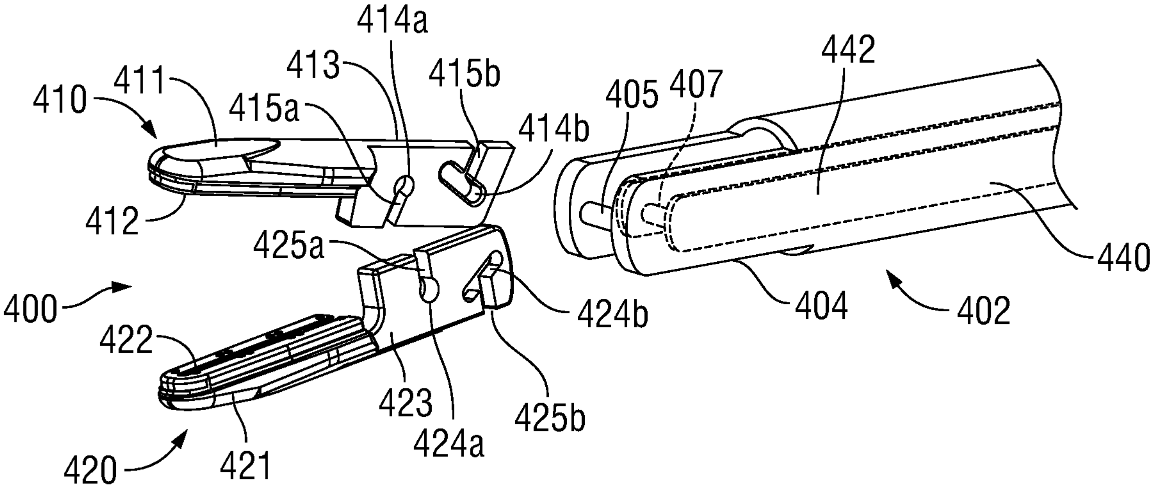
FIG. 5 is a perspective view of another end effector assembly configured for use with the forceps of FIG. 1 and shown with parts separated.

Referring to FIG. 5, another embodiment of an end effector assembly 400 configured for releasable engagement with a distal end 404 of a shaft 402 of a forceps, e.g., forceps 10 (FIG. 1), is shown generally including first and second jaw members 410, 420, each having a distal jaw portion 411, 421 supporting a respective tissue sealing plate 412, 422 thereon and a proximal flange 413, 423 configured to facilitate engagement of end effector assembly 400 to shaft 402. More specifically, proximal flanges 413, 423 of jaw members 410, 420, respectively, each include a pivot pin aperture 414*a*, 424*a* configured to receive pivot pin 405 therethrough, and an oppositely-angled cam slot 414*b*, 424*b* configured to receive and permit slidable translation of cam pin 407 therethrough. Further, proximal flanges 413, 423 each define a first mouth 415*a*, 425*a* in communication apertures 414*a*, 424*a*, respectively, to permit passage of pivot pin 405 therethrough and into engagement within apertures 414*a*, 424*a*, and a second mouth 415*b*, 425*b*, in communication with angled cam slots 414*b*, 424*b* to permit passage of cam pin 407 therethrough and into engagement within angled slots 414*b*, 424*b*.

Shaft 402 includes a bifurcated distal end 404 having pivot pin 405 extending transversely across bifurcated distal end 404 of shaft 402. Pivot pin 405 is fixedly mounted to or integrally formed with bifurcated distal end 404 of shaft 402. Drive bar 440 is slidably disposed within shaft 402, similarly as described above with respect to forceps 10 (FIGS. 1-3) and likewise includes a bifurcated distal member 442 having a cam pin 407 extending transversely across the bifurcated distal end 442 thereof. Cam pin 407 may be fixedly mounted or integrally formed with bifurcated distal member 442 of drive bar 440.

In order to engage jaw members 410, 420 of end effector assembly 400 to shaft 402, jaw members 410, 420 are manipulated such that pivot pin 405 of shaft 402 is inserted through first mouths 415*a*, 425*a* of jaw members 410, 420 and into engagement within apertures 414*a*, 424*a*. Likewise, jaw members 410, 420 are manipulated such that cam pin 407 of drive bar 440 is inserted through second mouths 415*b*, 425*b*, and into engagement within angled cam slots 414*b*, 424*b* of jaw members 410, 420, respectively. Mouths

415*a*, 425*a* and 415*b*, 425*b* may be configured similarly to coupling member 144 (FIG. 2), described above, such that pivot pin 405 and cam pin 407 can be snap-fit into engagement within respective apertures 414*a*, 424*a* and slots 414*b*, 424*b*.

Referring additionally to FIG. 1, with jaw members 410, 420 pivotably coupled to bifurcated distal end 404 of shaft 402 via pivot pin 405 and slidably and pivotably coupled to cam pin 407 of drive bar 440, which is ultimately coupled to movable handle 40, movable handle 40 may be manipulated to effect opening or closing of jaw members 410, 420, as desired. A knife 190 (FIG. 2) configured to releasably engage a knife drive sleeve 180 (FIG. 3) may also be provided for use with end effector assembly 400, similarly as described above. As can be appreciated, pivot pin 405 and cam pin 407 are not individual components separable from shaft 402 and, thus, reposable of end effector assembly 400 requires only jaw members 410, 420 for assembly, thereby reducing part count and minimizing accidental loss of individual components.

Figure 6:
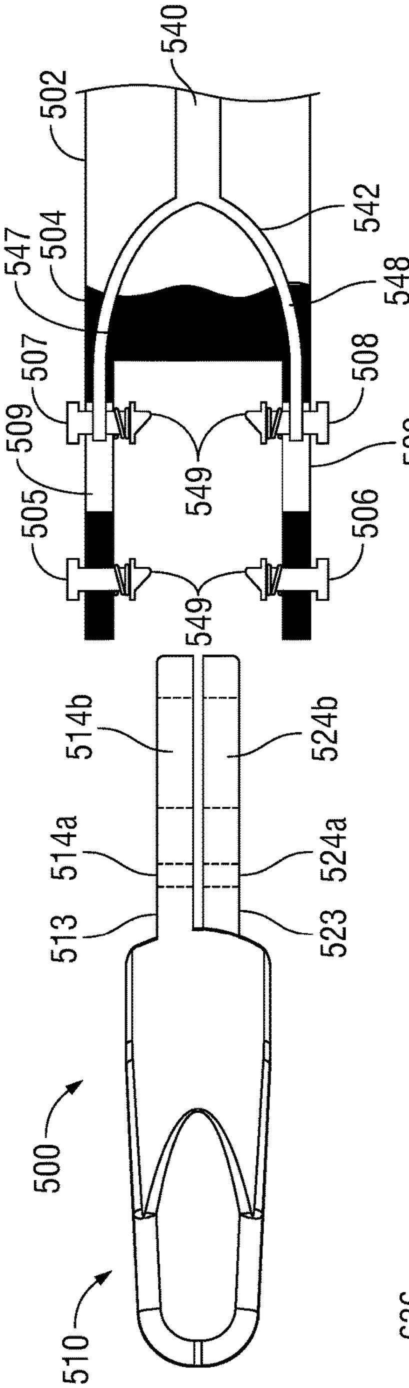
FIG. 6 is a top, longitudinal, cross-sectional view of another end effector assembly configured for use with the forceps of FIG. 1.

Turning now to FIG. 6, another embodiment of an end effector assembly 500 provided in accordance with the present disclosure and configured for releasably engagement with a distal end 504 of a shaft 502 of a forceps, e.g., forceps 10 (FIG. 1) is shown. End effector assembly 500 includes first and second jaw members 510 (similar to any of the jaw members described above), each having a proximal flange 513, 523 configured to facilitate engagement of end effector assembly 500 to shaft 502. Proximal flanges 513, 523, each include a pivot pin aperture 514*a*, 524*a* configured to receive a pivot pin 505, 506, respectively, and an oppositely-angled cam slot 514*b*, 524*b* configured to receive and permit slidable translation of a cam pin 507, 508, respectively, therethrough.

Shaft 502 includes a pair of spring-loaded pivot pins 505, 506 respectively mounted on each side of the bifurcated distal end 504 thereof. Shaft 502 further includes a pair of spring-loaded cam pins 507, 508 slidably mounted within longitudinal cam slots 454 defined within bifurcated distal end 504 thereof. Drive bar 540 includes a bifurcated distal member 542 including first and second arms 547, 548 engaged to spring-loaded cam pins 507, 508, respectively, to effect longitudinal translation of cam pins 507, 508 through longitudinal cam slots 509 defined within bifurcated distal end 504 of shaft 502 and angled cam slots 514*b*, 524*b* of jaw members 510 upon manipulation of movable handle 40 (FIG. 1). Bifurcated distal member 542 may be configured to releasably engage or fixedly connect to cam pins 507, 508. Each of spring-loaded pivot pin 505, 506 and spring-loaded cam pins 507, 508 has an inner most end defining an angled surface 549 configured for facilitate the outward urging of pins 505, 506, 507, 508 against the bias of the springs thereof upon contact with end effector assembly 500 to facilitate engagement therebetween, as will be described below.

To releasably engage end effector assembly 500 to shaft 502, the user approximates end effector assembly 500 and bifurcated distal end 504 of shaft 502 relative to one another such that proximal flanges 513, 523 of jaw members 510 are inserted between the bifurcated distal end 504 of shaft 502. Upon insertion of proximal flanges 513, 523 into bifurcated distal end 504 of shaft 502, flanges 513, 523 contact angled surfaces 549 of pivot pins 505, 506 and cam pins 507, 508 to urge pins 505, 506, 507*m* 508 outwardly against their bias, thus permitting further insertion of flanges 513, 523 into bifurcated distal end 504 of shaft 502. Flanges 513, 523 are inserted into bifurcated distal end 504 of shaft 502 until pivot pins 505, 506 are positioned adjacent pivot pin apertures 514*a*, 524*a*, thus allowing pivot pins 505, 506 to return under bias to their initial positions and into engagement within apertures 514*a*, 524*a* and such that cam pins 507, 508, once positioned adjacent cam slots 514*b*, 524*b* are returned under bias to their initial positions and into engagement within cam slots 514*b*, 524*b*, thus pivotably engaging jaw members 510 to shaft 502 and operably engaging jaw members 510 to drive bar 540. To disassemble end effector assembly 500, a tool (not shown) may be used to pull pivot pins 505, 506 and cam pins 507, 508 outwardly to disengage them from the proximal flanges 513, 523, thus permitting the removal of end effector assembly 500. The use and operation of end effector assembly 500 is similar to that described above with respect to the previous embodiments and, thus, will not be repeated here for purposes of brevity.

Figure 6A:
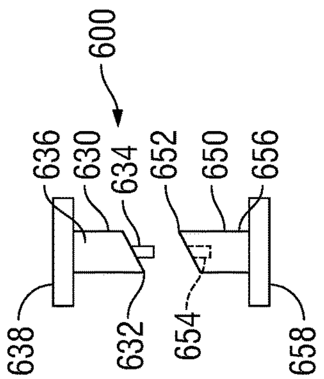
FIG. 6A is a schematic view of a pair of pins with locking features configured for use with the end effector assembly of FIG. 6.

As shown in FIG. 6A, pivot pins 505, 506 and/or cam pins 507, 508 (see FIG. 6) may alternatively have the configuration of pin assembly 600. Pin assembly 600 includes first and second pins 630, 650. Inner ends 632, 652 of pins 630, 650 include complementary engagement features 634, 654, e.g., male-female connectors, snap-fit connectors, friction-fit connectors, threaded connectors, etc., configured to engage one another to engage first and second pins 630, 650, respectively, to one another. First and second pins 630, 650, respectively, each further include a cap 638, 658 disposed about outer end 636, 656, respectively, thereof such that, upon engagement of first and second pins 630, 650 to one another, jaw members 510 may be operably engaged to shaft 502 and/or drive bar 540 (see FIG. 6) with pin assembly 600 extending therebetween and with caps 638, 658 disposed on either end thereof.

Figure 7:
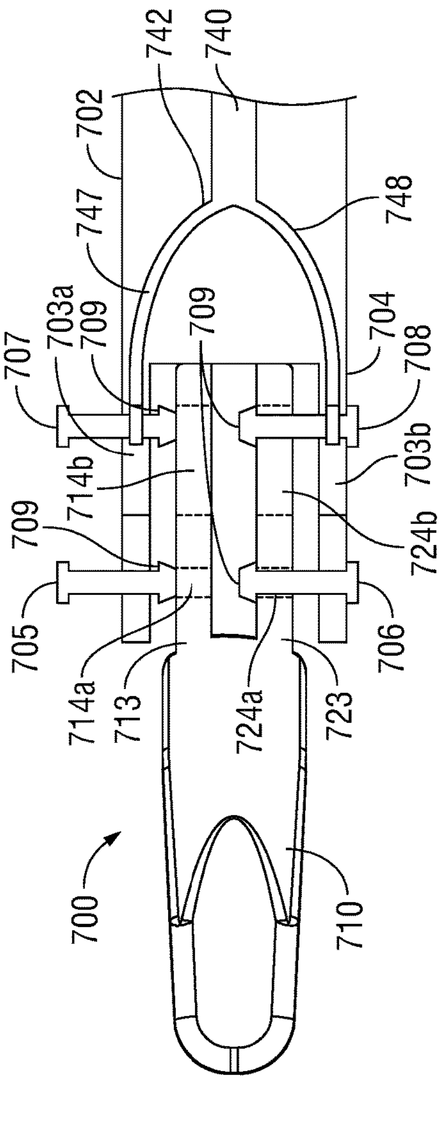
FIG. 7 is a top view of another end effector assembly configured for use with the forceps of FIG. 1.

Turning now to FIG. 7, another embodiment of an end effector assembly 700 similar to end effector assembly 500 (FIG. 6) and configured for releasable engagement with a shaft 702 of a forceps, e.g., forceps 10 (FIG. 1) is shown. End effector assembly 700 includes first and second jaw members 710 (similar to the jaw members of the end effector assemblies described above), each having a proximal flange 713, 723 configured to facilitate engagement of end effector assembly 700 to shaft 702. Proximal flanges 713, 723 each include an aperture 714*a*, 724*a* configured to receive a pivot pin 705, 706, respectively, and an oppositely-angled cam slot 714*b*, 724*b* configured to receive and permit slidable translation of a cam pin 707, 708, respectively, therethrough.

Shaft 702 includes pivot pins 705, 706 preloaded in aperture (or otherwise engaged to) bifurcated distal end 704 thereof on either side thereof and cam pins 706, 708 preloaded and slidably mounted within longitudinal cam slots 703*a*, 703*b* defined within bifurcated distal end 704 thereof. Pivot pins 705, 706 and cam pins 707, 708 each include snap-fit engagement features 709 disposed or monolithically formed at the free ends thereof that are configured to facilitate operable engagement of pivot pins 705, 706 and cam pins 707, 708 to flanges 713, 723 of jaw members 710 of end effector assembly 700. Drive bar 740 includes a bifurcated distal member 742 including first and second arms 747, 748 engaged to cam pins 707, 708, respectively, to effect longitudinal translation of cam pins 707, 708 through longitudinal cam slots 703*a*, 703*b* defined within bifurcated distal end 704 of shaft 702 and angled cam slots 714*b*, 724*b* of jaw members 710 upon manipulation of movable handle 40 (FIG. 1).

To releasably engage end effector assembly 700 to shaft 702, the user first introduces proximal flanges 713, 723 of jaw members 710 between bifurcated distal end 704 of shaft 702, aligns apertures 714*a*, 724*a* with pivot pins 705, 706, and aligns cam slots 714*b*, 724*b* with cam pins 707, 708. Next, the user urges pivot pins 705, 706 inwardly into apertures 714*a*, 724*a* such that engagement features 709 of pivot pins 705, 706 are translated completely through apertures 714*a*, 724*a* to snap-fit into engagement therewith, and likewise urges cam pins 707, 708 inwardly into cam slots 714*b*, 724*b* such that engagement features 709 of cam pins 707, 708 are translated completely through cam slots 714*b*, 724*b* and into snap-fit into engagement therewith. The use and operation of end effector assembly 700 is similar to that described above with respect to the previous embodiments and, thus, will not be repeated here for purposes of brevity.

Figure 8:
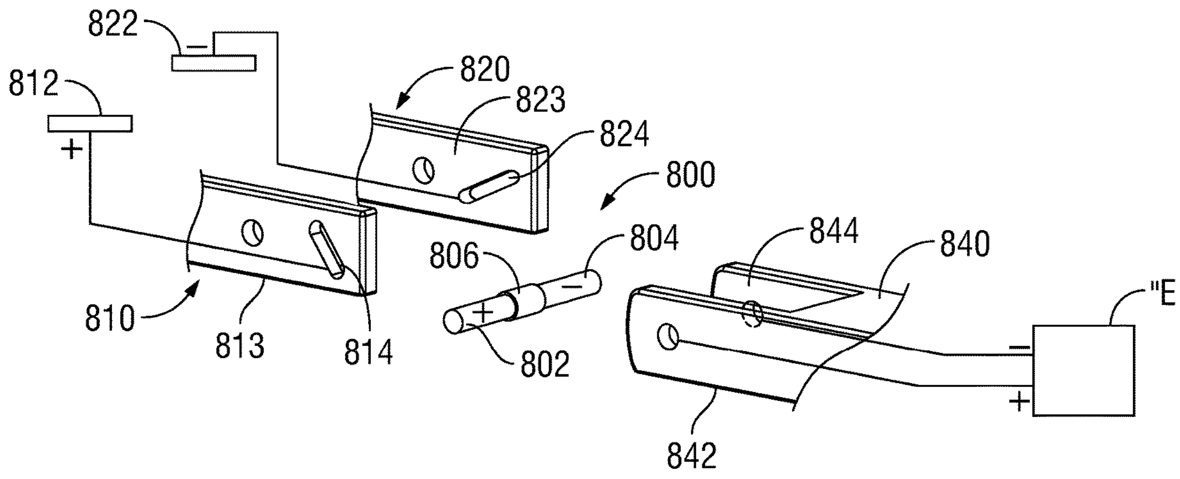
FIG. 8 is a schematic view of a cam pin configured for use the forceps of FIG. 1 and/or any of the end effector assemblies described herein.

Turning now to FIG. 8, a electrical connector cam pin 800 configured for use with any of the end effector assemblies described above (or any other suitable releasably engagable end effector assembly) for establishing electrical communication between the drive bar (or other portion of the surgical instrument) and the releasably engagable end effector assembly (or portion thereof) is shown. Cam pin 800 includes a first electrically conductive portion, e.g., positive portion 802, at a first end thereof, a second electrically conductive portion, e.g., negative portion 804, at a second end thereof, and an insulative portion 806 disposed therebetween that electrically insulates positive and negative portions 802, 804, respectively, from one another. In use, similarly as described above, cam pin 800 is engaged within first and second cam slots 814, 824 of proximal flanges 813, 823 of jaw members 810, 820, respectively (which are electrically coupled to sealing plates 812, 822, respectively, thereof) and is also engaged between first and second first and second bifurcated portions 842, 844, respectively, of drive bar 840 (which are electrically insulated from one another and adapted to connect to the respective positioned and negative terminals of the energy source "E"). First and second jaw members 810, 820 are electrically insulated from one another, e.g., via insulative coating or insulative materials (not explicitly shown) disposed at the interface therebetween. Thus, first and second electrically conductive portions 802, 804 of cam pin 800 can be used to transmit bipolar energy from the surgical instrument (via drive bar 840) to jaw members 810, 820 (via proximal flanges 813, 823), as will be described below.

Upon assembly, e.g., upon engagement of jaw members 810, 820 to the shaft (not shown) and drive bar 840, similarly as described with respect to any of the embodiments above, jaw member 810 is electrically coupled to first bifurcated portion 842 of drive bar 840 (which is ultimately connected to a positive terminal of an energy source "E") via positive portion 802 of cam pin 800 and jaw member 820 is electrically coupled to second bifurcated portion 844 of drive bar 840 (which is ultimately connected to a negative terminal of energy source "E") via negative portion 804 of cam pin 800. Thus, sealing plates 812, 822 of jaw members 810, 820, respectively, can be charged to different potentials for supplying bipolar electrosurgical energy to tissue grasped therebetween to treat tissue grasped therebetween. As can be appreciated, the electrical connector cam pin 800 obviates the need for separate electrical connections, e.g., wires, that require coupling and de-coupling upon engagement and disengagement.

Figure 9:
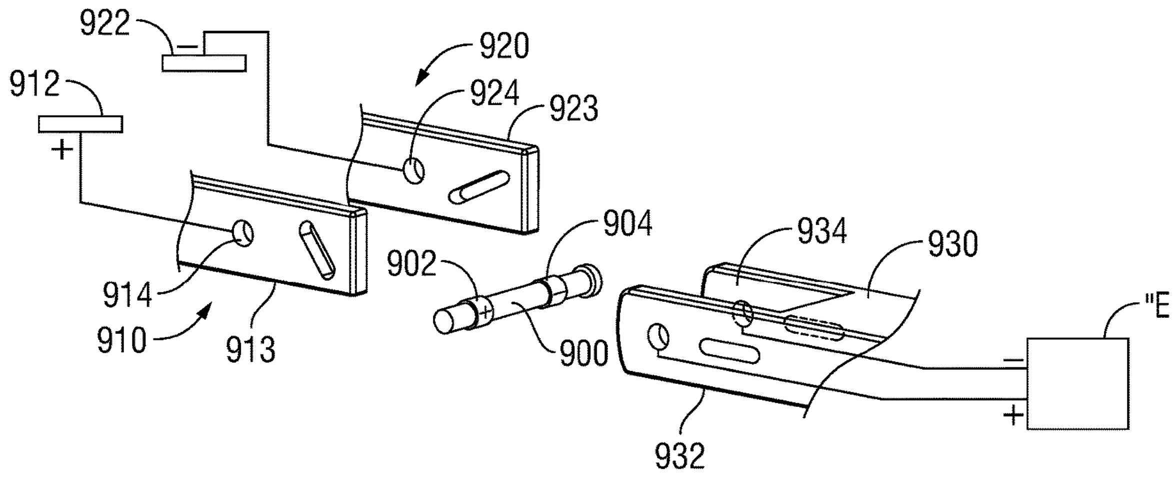
FIG. 9 is a schematic view of a pivot pin configured for use with the forceps of FIG. 1 and/or any of the end effector assemblies described herein.

Turning now to FIG. 9, a electrical connector pivot pin 900 configured for use with any of the end effector assemblies described above (or any other suitable releasably engagable end effector assembly) for establishing electrical communication between the shaft 930 (or other portion of the surgical instrument) and the releasably engagable end effector assembly (or portion thereof) is shown. Pivot pin 900 is formed from an electrically-insulative material and includes a first electrically conductive sleeve, e.g., positive sleeve 902, disposed towards a first end thereof, and a second electrically conductive sleeve, e.g., negative sleeve 904, spaced-apart from first sleeve 902 and disposed towards a second end of pivot pin 900 such that positive and negative sleeves 902, 904, respectively, are electrically insulated from one another. Alternatively, pivot pin 900 may be configured similarly to cam pin 800 (FIG. 8), or vice versa.

In use, similarly as described above, pivot pin 900 is engaged within apertures 914, 924 of proximal flanges 913, 923 of jaw members 910, 920, respectively, and is also engaged between first and second first and second bifurcated portions 932, 934, respectively, of shaft 930. At least a portion of each of jaw members 910, 920 is electrically-conductive and electrically coupled to sealing plate 912, 922 thereof. Jaw members 910, 920 are also electrically insulated from one another as are first and second bifurcated portions 932, 934 of shaft 930. As such, upon engagement of jaw members 910, 920 to shaft 930, e.g., similarly as described with respect to any of the embodiments above, jaw member 910 is electrically coupled to first bifurcated portion 932 of shaft 930 (which is ultimately connected to a positive terminal of an energy source "E") via positive sleeve 902 of cam pin 900 and jaw member 920 is electrically coupled to second bifurcated portion 934 of shaft 930 (which is ultimately connected to a negative terminal of energy source "E") via negative sleeve 904 of cam pin 900. Thus, sealing plats 912, 922 of jaw members 910, 920 can be charged to different potentials for supplying bipolar electrosurgical energy to tissue grasped therebetween to treat tissue grasped therebetween. As can be appreciated, the electrical connector pivot pin 900 obviates the need for separate electrical connections, e.g., wires, that require coupling and de-coupling upon engagement and disengagement.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical forceps, comprising:

a housing including a drive mechanism;

a shaft extending distally from the housing, a distal portion of the shaft including a pivot pin;

a drive bar slidably disposed at least partially within the shaft, a proximal portion of the drive bar operably coupled to the drive mechanism such that actuation of the drive mechanism effects longitudinal translation of the drive bar, a distal portion of the drive bar including a cam pin; and an end effector assembly including a first jaw member and a second jaw member, the first jaw member movable relative to the second jaw member between a spaced-apart position and an approximated position for grasping tissue therebetween, the first jaw member including a proximal flange defining a pivot aperture, a first mouth providing access to the pivot aperture, a cam slot, and a second mouth providing access to the cam slot, the pivot pin configured to pass through the first mouth and into the pivot aperture to engage the first jaw member with the shaft, the cam pin configured to pass through the second mouth and into the cam slot to engage the first jaw member with the drive bar, wherein the first mouth extends from the pivot aperture to a first edge of the first jaw member and the second mouth extends from the cam slot to a second edge of the first jaw member, the first edge opposite the second edge.

2. The surgical forceps according to claim 1, wherein the pivot pin is configured to releasably engage the pivot aperture.

3. The surgical forceps according to claim 1, wherein the cam pin is configured to releasably engage the cam slot.

4. The surgical forceps according to claim 1, wherein the second jaw member includes a proximal flange.

5. The surgical forceps according to claim 4, wherein the proximal flange of the second jaw member defines a second pivot aperture configured to engage the pivot pin.

6. The surgical forceps according to claim 5, wherein the proximal flange of the second jaw member defines a second cam slot configured to engage the cam pin.

7. The surgical forceps according to claim 6, wherein the proximal flange of the second jaw member defines a third mouth providing access to the second pivot aperture.

8. The surgical forceps according to claim 7, wherein the proximal flange of the second jaw member defines a fourth mouth providing access to the second cam slot.

9. The surgical forceps according to claim 1, wherein the first jaw member includes a first surface having a tissue sealing plate, and a second surface disposed opposite the first surface.

10. The surgical forceps according to claim 9, wherein the second mouth of the first jaw member extends through the second surface of the first jaw member.

11. The surgical forceps according claim 8, wherein the first jaw member includes a first surface having a tissue sealing plate and a second surface disposed opposite the first surface, wherein the second jaw member includes a third surface having a sealing plate and a fourth surface disposed opposite the third surface, wherein the second mouth of the first jaw member extends through the second surface of the first jaw member, and wherein the fourth mouth of the second jaw member extends through the fourth surface of the second jaw member.

12. The surgical forceps according to claim 1, wherein the first mouth extends from the pivot aperture in a first direction, and the second mouth extends from the cam slot in a second direction, the first direction being opposite from the second direction.

13. The surgical forceps according to claim 1, wherein the pivot pin is disposed distally of the cam pin.

14. An end effector for use with a surgical instrument, the end effector comprising:

a first jaw member including:

a first pivot aperture;

a first mouth extending from the first pivot aperture;

a first cam slot; and a second mouth extending from the first cam slot, the first pivot aperture configured to engage a pivot pin of the surgical instrument, and the first cam slot configured to engage a cam pin of the surgical instrument; and a second jaw member disposed in pivotal relation with the first jaw member, the second jaw member including:

a second pivot aperture;

a third mouth extending from the second pivot aperture;

a second cam slot; and a fourth mouth extending from the second cam slot;

the second pivot aperture configured to engage the pivot pin of the surgical instrument, and the second cam slot configured to engage the cam pin of the surgical instrument, wherein the first mouth of the first jaw member is parallel to the second mouth of the first jaw member.

15. The end effector according to claim 14, wherein the first mouth of the first jaw member extends between the first pivot aperture and a first edge of the first jaw member.

16. The end effector according to claim 15, wherein the second mouth of the first jaw member extends between the first cam slot and a second edge of the first jaw member.

17. The end effector according to claim 14, wherein the first mouth of the first jaw member extends from the first pivot aperture in a first direction, wherein the second mouth of the first jaw member extends from the first cam slot in a second direction, the first direction being opposite from the second direction.

18. The end effector according to claim 14, wherein the first mouth of the first jaw member extends from the first pivot aperture in a first direction, wherein the third mouth of the second jaw member extends from the second pivot aperture in a second direction, the first direction being opposite from the second direction.

19. The end effector according to claim 14, wherein the first cam slot of the first jaw member is angled in a first direction relative to the second mouth of the first jaw member, the second cam slot of the second jaw member is angled in a second direction relative to the second mouth of the second jaw member, the first direction being a mirror image of the second direction.

* * * * *